(12) United States Patent
Cronshaw et al.

(10) Patent No.: US 6,275,603 B1
(45) Date of Patent: Aug. 14, 2001

(54) METHOD AND APPARATUS FOR DETECTING GLASS PARTICLES IN GLASS BOTTLES FILLED WITH BEER

(75) Inventors: Anthony James Cronshaw; Christopher James Hodges, both of Cambridge; Mark Robson Humphries, Saffron Walden; David Livingstone, Royston; Stephen Peter Woodall, Cheshire, all of (GB); Bernardus Cornelis Johannes Landman, Boskoop (NL)

(73) Assignee: Heineken Technical Services B.V., Amsterdam (NL)

( * ) Notice: Subject to any disclaimer, the term of this patent is extended or adjusted under 35 U.S.C. 154(b) by 0 days.

(21) Appl. No.: 09/051,663

(22) PCT Filed: Feb. 1, 1996

(86) PCT No.: PCT/NL96/00049

§ 371 Date: Jun. 24, 1998

§ 102(e) Date: Jun. 24, 1998

(87) PCT Pub. No.: WO97/14956

PCT Pub. Date: Apr. 24, 1997

(30) Foreign Application Priority Data

Oct. 18, 1995 (GB) .................................................. 9521285

(51) Int. Cl.[7] ...................................................... G06K 9/00
(52) U.S. Cl. ....................................... 382/142; 250/223 B
(58) Field of Search .............................. 348/86, 125, 127, 348/448; 356/240, 237; 250/223 B; 382/142, 141, 143, 149, 151, 152, 153

(56) References Cited

U.S. PATENT DOCUMENTS

| 3,777,169 | 12/1973 | Walter et al. . |
| 4,050,824 | 9/1977 | Woodrow et al. . |
| 4,172,524 | 10/1979 | Holm et al. . |
| 4,605,851 | 8/1986 | Ometz et al. . |
| 4,853,970 | * 8/1989 | Ott et al. ............................... 382/286 |
| 5,734,467 | * 3/1998 | Lucas ................................... 356/240 |

FOREIGN PATENT DOCUMENTS

| 0 086 143 | 8/1983 | (EP) . |
| WO 92/14142 | 8/1992 | (WO) . |

* cited by examiner

*Primary Examiner*—Joseph Mancus
*Assistant Examiner*—Vikkram Bali
(74) *Attorney, Agent, or Firm*—Pearne & Gordon LLP (57) ABSTRACT

This invention provides a method and apparatus (100) for detecting small glass particles (12) in bottles (1) filled with beer (10). The beer (10) is caused to rotate with respect to the bottle (1), and successive images are obtained from the bottle by means of a CCD-camera (40) which is arranged such that its optical axis (41) makes an angle α of about 135° with the axis (13) of the bottle (1), which is illuminated from below. The successive images are subtracted from each other to detect refracted light emanating from glass particles. These measurements are repeated a plurality of times. The invention thus offers an improvement in sensitivity and reliability of a detecting method. An apparatus (100) comprises a carousel (103) with a plurality of cameras dedicated to a single bottle. A system is described to reduce costs by having eight cameras share one image processing unit.

25 Claims, 3 Drawing Sheets

METHOD AND APPARATUS FOR DETECTING GLASS PARTICLES IN GLASS BOTTLES FILLED WITH BEER

The present invention relates to a method as for example disclosed in U.S. Pat. No. 3,777,169, and an apparatus for detecting glass particles in glass bottles filled with a beverage such as beer.

Various methods for detecting foreign particles in a fluid contained in a transparant container have already been proposed. An important category of such methods uses at least one camera to obtain an image from the container and its contents, and an image processing technique is used to process the image obtained by the camera in order to determine whether or not foreign (i.e. unwanted) particles are present in the fluid. In order for the image processing facilities to be able to distinguish between an image obtained from the container on the one hand, and an image obtained from a particle in the fluid, a specific spin/stop technique has been proposed. Herein, the container is firstly made to rotate about its longitudinal axis with a rotation speed and for a time sufficient to cause the fluid in the container to rotate with the container (referred to as "spin"). Secondly, the rotation of the container is abrubtly stopped; the fluid, however, continues to rotate. Subsequently, two images of the container and its contents are obtained, and these two images are subtracted from each other. Since the rotation of the container has stopped, the details in the images which originate from the container will be identical in both images, and will cancel each other by subtraction. On the other hand, the details in the images which originate from the fluid, or from foreign particles in the fluid, will be displaced with respect to each other in both images, such that they will remain visible after subtraction.

For obtaining an image of the container and its contents, various setups have been proposed.

Some of these techniques, as for example disclosed in WO-A-92/14142, can be considered as "transmission mode": herein, light from a light source travels through the container under investigation, and the camera is disposed opposite to the source, such that the axis of the camera makes an angle of 180° with the axis of the light source. Other techniques can be considered as "reflection back mode": herein, light from a light source is reflected back by the container and its contents to a camera which is disposed adjacent to the light source, such that the axis of the camera makes a small angle, usually in the range of 0° to 30°, with the axis of the light source.

A variant of these latter techniques can be considered as "reflection sideways mode": herein, light from a light source is reflected sideways back by the container and its contents to a camera which is disposed such that the axis of the camera makes an angle of substantially 90° with the axis of the light source. Such a setup also is disclosed in U.S. Pat. No. 3,777,169 or in U.S. Pat. No. 4,172,524.

Methods of the above indicated types have been utilized with varying degrees of success in a number of fields, such as the pharmaceutical industry. The present invention is directed to the field of beverages in bottles, and more particular bottles filled with beer. Hereinafter, the invention will be explained with reference to beer, but it is to be kept in mind that the same problems and the same solutions are applicable to other beverages, such that the scope of the invention also extends to such beverages.

An important aspect in the quality control when producing bottles filled with beer is detecting the presence of glass particles. It will be evident that the presence of glass particles in a beverage intended for human consumption is unacceptable, and a bottle containing such particles is to be considered as waste. Even though quality control has been a matter of constant attention in this field, none of the methods of the types described above have proved to be successful in a sufficient degree in the detection of small glass particles in beer. Especially very small particles, in the order of 0.2 mm, have proved to be very difficult to detect: known methods and apparatus and in particular those disclosed in U.S. Pat. No. 3,777,169 and WO-A-92/14142 do not detect these particles with a satisfying degree of certainty and reliability.

The cause of the unsatisfying performance of the methods and apparatus as available today can be attributed to a number of problems which are specifically involved with bottles of beer.

A first category of problems relates to the shape of the bottles. The bottom of a beer bottle, as seen from the inside of the bottle, is not flat or concave, such as in ampules as used in the pharmaceutical or medical field, but is convex. In other words, when the bottle stands upright, its bottom surface has the shape of a hill centered in the bottle. Because of this shape, glass particles tend to collect near the edge of the bottom, i.e. in the corner defined between the foot of said hill and the side wall of the bottle. In this position, glass particles are very difficult to detect in view of the optical characteristics of this portion of the bottle. On the one hand, the glass is curved relatively sharply in this area. On the other hand, the outside bottom is provided with a specific profile near the circumference, referred to as "knurling", and the bottle shows scuff marks in the lower part of the outside sidewall, often to such extent that this portion of the wall may ultimately be rendered untransparent for the purposes of imaging. This may be further exacerbated by the presence of mould marks from the bottle forming process.

A second category of problems relates to the nature of the fluid in the bottle. Beverages such as beer contain a certain amount of dissolved gas, usually $CO_2$, which causes bubbles to be generated when the fluid is disturbed. These bubbles tend to interfere with the optical detection methods. It will be evident that the detection methods should be able to discriminate between unwanted glass particles and $CO_2$ bubbles, or otherwise too many "correct" bottles will be rejected due to perfectly harmless objects, such as for instance $CO_2$ bubbles or other dissolved gases.

It is a general object of the invention to provide improved method and apparatus with an improved detection efficiency and reliability for glass particles in bottles filled with a beverage such as beer, in which the above-mentioned problems are overcome.

More particularly, it is an object of the invention to provide such detection method and apparatus suitable for detecting glass particles as small as 0.2 mm. Preferably, the method and apparatus should be able to detect glass particles in the range of 0.2 mm to 10 mm (or larger). In this respect it is observed that the upper limit of the size of the particles which can be expected to be present in bottles at all, is determined by the diameter of the mouth of the bottle.

Yet more particularly, it is an object of the invention to provide such detection method and apparatus capable of meeting the above demends, also suitable for implementation in a production line for producing filled bottles in a product plant without affecting the production speed in a negative way.

It is a further object of the invention to fulfill the above requirements in a cost-efficient way.

The above objectives are obtained by a method of detecting the presence of glass particles in a bottle filled with a beverage such as beer, the bottle (1) having a bottom (4) with a central, inwardly directed convex portion (6); the method comprising the steps of:

a) causing the beverage (10) in the bottle (1) to rotate with respect to the bottle (1);

b) holding the bottle (1) stationary with respect to a camera (40);

c) illuminating the bottle (1) with a light bundle (31) impinging on the bottom (4) of the bottle (1), the direction (32) of the bundle (31) being substantially aligned with the direction of the central axis (13) of the bottle (1);

d) directing the camera (40), preferably a CCD-camera, such that an optical axis (41) of the camera (40) makes an angle α in the range of 120°–150°, preferably substantially 135°, with the direction (32) of the bundle (31);

e) obtaining a first image signal representative for a first image obtained by the camera (40);

f) obtaining a second image signal representative for a second image obtained by the camera (40), the second image being obtained at a moment in time differing from the moment in time the first image was obtained;

g) comparing the first and second image signals to obtain a compared signal;

h) repeating the steps (e)–(g) at least once;

i) generating a bottle reject signal if at least one of the compared signals obtained in step (h) indicates the presence of a moving object.

The above objectives likewise are obtained by a production line (200) for filling bottles (1) with a beverage such as beer, each bottle (1) having a central axis (13) and a bottom (4) showing a central, inwardly directed convex portion (6); the production line (200) comprising a detecting apparatus, a first transportation means (201) for transporting the filled bottles (1) towards the detecting apparatus (100) and a second transportation means (202) for transporting the checked bottles (1) away from the detecting apparatus (100);

the detecting apparatus (100) comprising:

a carousel (103) which is rotatably mounted with respect to the fixed world;

a plurality of detecting stations (20) fixed to said carousel (103), each detecting station (20) comprising:

a subframe (21);

holding means (22) for accepting and holding a bottle (1) in an upright position stationary with respect to said subframe (21);

an illumination device (30) for generating a bundle of visible light (31) and to direct this bundle (31) in a direction (32) substantially aligned with the direction of said central axis (13) of an accepted bottle (1) held by said holding means (22);

a camera means (40), preferably a CCD-camera, fixed to said subframe (21), an optical axis (41) of the camera (40) being directed such that it makes an angle α in the range of 120° to 150° with the direction (32) of the bundle (31) and intersects the central axis (13) of said accepted bottle (1) at a point S which is located near the top of the hill portion (6);

the apparatus (100) further comprising:

at least one image processing unit (50), a central processing unit (130), and a reject device (120) associated with said second transportation means (202), each image processing unit (50) being adapted to receive at least two successive image signals from a camera (40), to compare these signals, to provide a compared signal, and to communicate said compared signal to said central processing unit (130), said central processing unit (130) being adapted to control said reject device (120) such as to remove rejected bottles from said second transportation means (202).

The above-mentioned and other aspects, features and advantages of the present invention will become more apparent from the following description of a preferred embodiment with reference to the drawings, in which.

Figure 1:
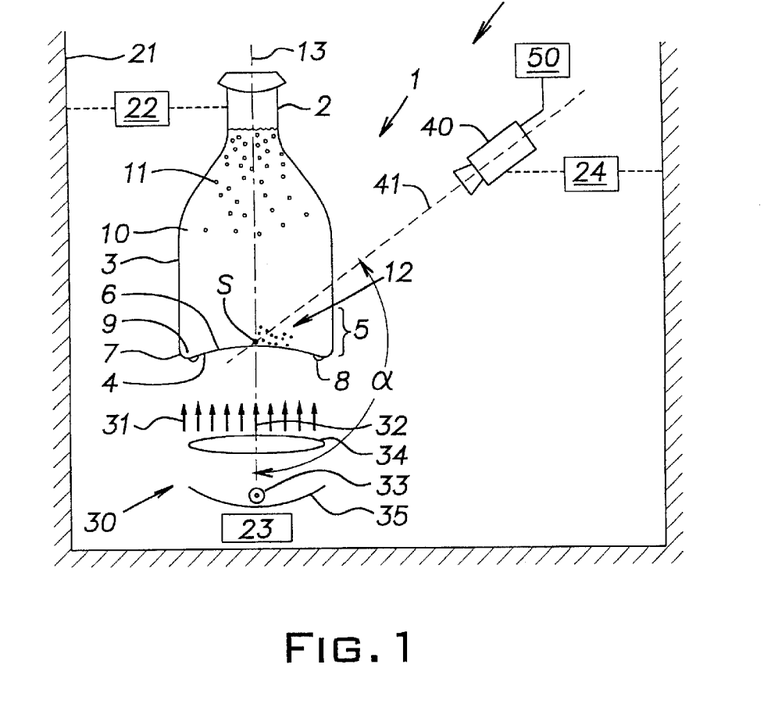
FIG. 1 schematically illustrates a setup for detecting glass particles in a bottle of beer according to the invention.

FIG. 1 schematically shows a beer bottle 1 having a central body axis 13, a neck portion 2, a substantially cylindrical side wall 3, and a bottom 4. A lower portion 5 of the side wall 3 usually has scuff marks, which reduce the optical quality of the glass in this portion; this lower portion 5 will also be referred to as "scuff portion". A central part 6 of the bottom 4 is convex to the inside of the bottle 1, i.e. it has the shape of a small hill; this central part 6 will also be referred to as "hill portion". The bottom 4 has a rim 7, the underside of which is provided with a profile or "knurling" 8. At this rim 7, said hill portion 6 of the bottle 1 meets the scuff portion 5 of the bottle 1, defining a corner 9. The bottle 1 is filled with beer 10, which may contain $CO_2$ bubbles 11.

FIG. 1 shows the beer bottle 1 at an inspection station 20 for inspecting the bottle 1 on the presence of glass particles 12. The inspection station 20 comprises a machine subframe 21. The bottle 1 is firmly held stationary with respect to the subframe 21, by holding means which are generally indicated at 22, which engage the neck portion 2 of the bottle 1. The construction of these holding means 22 is not critical to the present invention, and detailed knowledge thereof will not be necessary for a skilled person for understanding the present invention; therefore, these holding means 22 will not be discussed in greater detail.

The inspection station 20 comprises an illumination device 30 fixed to the subframe 21 by any suitable fixing means 23. The illumination device 30 is adapted to generate a bundle of visible light 31 and to direct this bundle 31 to the bottom 4 of the bottle 1 in a direction 32 which substantially is aligned with the central axis 13 of the bottle 1. The width of the bundle 31 is sufficient to illuminate the hill portion 6, and preferably is sufficient to illuminate the bottom 4 completely. The nature and construction of this illumination device 30 is not critical to the present invention, and detailed knowledge thereof will not be necessary for a skilled person for understanding the present invention; therefore, a detailed description of this illumination device 30 is omitted. Suffice it to say that the illumination device 30 may comprise a bright light source 33, such as a laser or a halogen lamp, and optical means 34, 35 for shaping and directing the light bundle 31, such as a lens 34 and a mirror 35.

The inspection station 2C further comprises a camera means 40, preferably a CCD-camera. The camera 40 is fixed to the subframe 21 by any suitable fixing means 24. Thus, and according to an important aspect of the present invention, the bottle 1 is held firmly stationary with respect to the camera 40. The camera 40 has an optical axis 41 which, according to a further important aspect of the invention, makes an angle α in the range of 120° to 150° with the direction 32 of the bundle 31. Preferably, this angle α is substantially equal to 135°, as illustrated in FIG. 1. The optical axis 41 of the camera 40 intersects the central axis 13 of the bottle 1 at a point S which is located near the top of the hill portion 6. In practice, this intersection point S may be located a short distance above the top of the hill portion 6, as illustrated. Preferably, the camera 40 is set such that the focal point or focal plane substantially coincides with said intersection point S. Optics may be chosen to ensure a relatively long depth of field in the direction of the optical axis of the image capturing configuration, wherein the depth of field may be chosen in relation to the dimensions of the bottle 1.

It is observed that the camera 40 itself may be disposed at a different place and/or under a different angle, while the optical axis of the camera may be directed to the bottle 1 in the way as shown by means of optical means such as mirrors. However, in order to eliminate the influence of possible machine vibrations as much as possible, such optical deflection means are not preferred; instead, it is preferred that the camera 40 receives light from the bottle 1 directly, i.e. without any intermediary optical deflection means.

It is further observed that, in order to prevent as much as possible the occurence of vibrations of the bottle 1 due to the influence of possible machine vibrations, the underside of the bottle 1, for instance the scuff portion 5, may be supported with respect to the subframe 21 by any suitable support means, which, however, is not illustrated in FIG. 1 for the sake of simplicity.

The above-mentioned setup of the inspection station 20 offers important advantageous features, which promote that glass particles 12, if any are present, will be detected by the camera 40 with preference. This can be understood as follows. Normally, light 31 will pass the bottom 4 of the bottle 1 undisturbed, i.e. no light, or at most a very small fraction of the light, will be refracted in the direction α, i.e. towards the camera 40. Further, only little light will impinge on the wall 3 at the location where the wall 3 is intersected by the optical axis 41 of the camera 40, so the wall 3 itself will send virtually no light at all towards the camera. In fact, the camera 40 "looks" to the top of the hill portion 6 without being disturbed by possible scuff marks, because the optical axis 41 of the camera 40 intersects the wall 3 at a point well above the scuff portion 5, and further without being disturbed by possible bubbles 11, because any bubbles 11 in the beer 10 will tend to drift upwards, out of the zone "seen" by the camera 40. Therefore, under normal circumstances, virtually no light will reach the camera 40, i.e. the camera generates a "dark" image. At worst, the camera 40 will receive only very weak light signals originating from the bottle 1.

On the other hand, solid particles such as glass particles will tend to collect near the bottom 4 under the influence of gravity. Glass particles are capable of refraction, i.e. to allow a light ray to pass yet altering its direction by refraction when such light ray crosses the beer-glass interface and subsequently crosses the glass-beer interface. By virtue of this refraction capability, some of the light impinging on the glass particle may be deviated over 45° from its original direction, in the direction towards the camera 40, in which case the camera 40 receives a strong light signal. In other words, the invention advantageously utilizes an optical feature of glass particles, i.e. the capability of refraction, for stimulating that substantially only light signals originating from glass particles will reach the camera 40. As a result, glass particles 12 cause a stronger signal at the camera 40 than bottle portions do. This technique can be considered as "refraction mode".

As mentioned above, the bottle 1 is kept stationary with respect to the camera 40. In contrast, the beer 10 in the bottle 1 is caused to perform a rotation in the bottle 10, as will be explained in more detail. Due to this rotationary motion of the beer 10 in the bottle 1, glass particles 12, if present, will be caused to follow a rotationary path within the bottle 1. An important aspect in this respect is that such particles move with respect to the camera 40. Consequently, in two successive images obtained by the camera 40, such particles will have different positions. Such two images can be processed, for instance by subtraction, which eliminates the stationary image contributions originating from the stationary bottle, while the image contributions originating from the moving particles are highlighted.

Such a technique is known per se. However, the accuracy of this technique is improved in accordance with the present invention. In view of the fact that detection is performed in the refraction mode, as characterized by the orientation angle α of the camera, image contributions originating from the bottle in principle are weaker than image contributions originating from glass particles. Further, in view of the fact that the camera 40 looks primarily to the region in the immediate vicinity of the top of the hill portion 6 of the bottom 4, while avoiding the scuff portion 5 of the bottle wall 3, the number of image contributions originating from the bottle will be relatively small, while further $CO_2$ bubbles 11 will generate substantially no image contributions because these bubbles tend to migrate upwards, away from the field of view of the camera. As a result of these facts, in combination with the fact that the bottle 1 is kept rigidly stationary with respect to the camera 40, image contributions which do not originate from glass particles are eliminated from the images by the subtraction technique to a larger extent than in prior art techniques. In turn, this implies that the detection technique of the present invention is more sensitive to small particles (particles as small as 0.2 mm or even smaller) than prior art techniques.

As mentioned above, the bottle 1 is held stationary in the station 20, and the beer 10 in the bottle 1 has a rotationary motion with respect to the bottle 1 when the bottle 1 is in the station 20. The beer 10 has obtained this motion by means of the spin/stop-technique which is known per se: the bottle 1 is made to rotate by means of a rotating device, and subsequently the rotation of the bottle 1 is stopped. The rotating device may grab the bottle 1 by the neck portion 2; alternatively, the rotating device may comprise a belt system with belts acting on the side wall 3 of the bottle. However, the construction of the rotating device is not a subject of the present invention, and knowledge thereof is not necessary for a skilled person in order to understand the present invention. Moreover, such rotating devices are known per se. Therefore, the constructional details of a rotating device are not described in detail, and the rotating device is not illustrated in the drawings for the sake of simplicity.

When spinning the bottle 1, the spinning bottle 1 acts on the beer 10 such as to impart a rotationary flow on the beer. Now, two effects occur which are worth mentioning. First, the flowing beer induces movement of the glass particles 12, if such are present. Second, $CO_2$ bubbles 11 may be generated in the disturbed beer 10.

The path of the moving glass particles 12 in the bottle 1 is relatively complex, because each glass particle is subjected to three forces:

the drag force executed by the rotating beer will force the glass particles to follow a path of revolution around the axis 13;

the centrifugal force will force the glass particles towards the side wall 3 of the bottle 1;

the gravity force will force the glass particles downwards, towards the bottom 4.

As a result, the glass particles will tend to collect in the corner 9, where at least the smaller particles (ca. 0.2 mm) are virtually invisible. In order to make also these small glass particles visible to the camera 40, they must be forced to move towards the centre of the bottom 4, i.e. they must "climb" the hill portion 6. The force responsible for such a movement is generated when the rotational movement of the beer slows down, and is generated by a flow in the beer which occurs due to the pressure difference between the fluid near the wall 3, where the fluid level and hence the fluid pressure is higher, and the fluid near the axis 13, where the fluid level and hence the fluid pressure is lower. Said flow should be sufficiently strong for forcing the small glass particles uphill; on the other hand, said flow should be not so extremely strong that glass particles, when they reach the axis 13, are forced upward and mix with the $CO_2$ bubbles. Preferably, the glass particles should migrate relatively gently toward the center of the hill portion 6, while at the same time the $CO_2$ bubbles are allowed to float upward and leave the field of view of the camera. It is noted that, generally speaking, the larger particles need not necessarily be moved up the hill, at least not completely, because they produce relatively strong signals which are well visible, even when such particles are situated in the corner 9.

With respect to the generation of $CO_2$ bubbles, the invention seeks to perform the spin/stop technique in such a way, that as little $CO_2$ bubbles as possible are generated.

Figure 2:
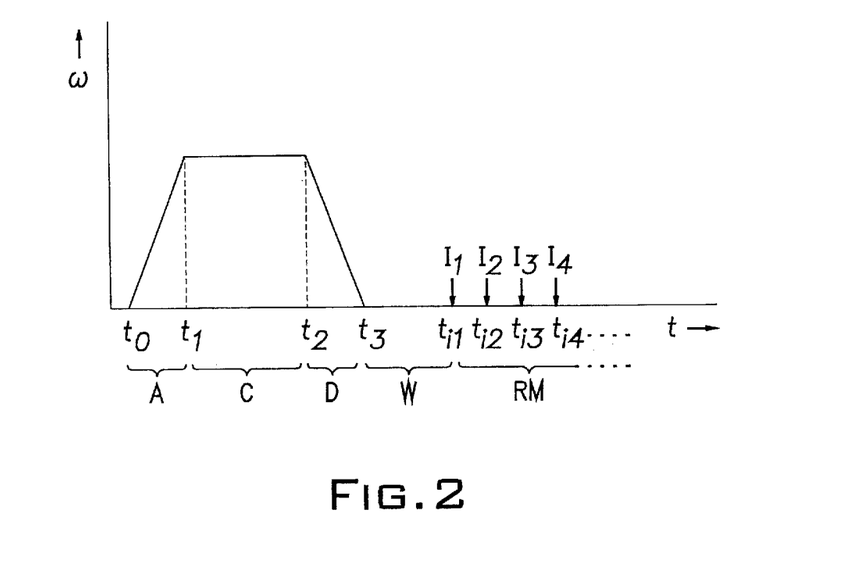
FIG. 2 is a timing diagram, illustrating the actions according to the present invention.

In the following, the improved spin/stop technique according to a preferred embodiment of the invention, which attaines the above objectives, will be described with reference to FIG. 2, in which the abscissa represents the time (t), and the ordinate represents the spin speed ($\omega$).

The spin/stop technique is preferably executed as follows:
1) At $t=t_0$, the bottle is accelerated with a substantially constant acceleration to a spin speed of 1000 revolutions per minute; this acceleration takes about 0.1 seconds. This phase is indicated as "acceleration phase A".
2) At $t=t_1$, the acceleration is stopped, and the spin speed is maintained constant at 1000 rpm for about 0.7 sec. This phase is indicated as "constant phase C".
3) Starting at $t=t_2$, the bottle is brought to a stop with a substantially constant deceleration in about 0.1 seconds. This phase is indicated as "deceleration phase D".
4) After the bottle has come to a stop ($t_3$), possible glass particles are allowed some time $t_w$ to migrate up the hill portion 6, while the $CO_2$ bubbles are allowed some time to float upward, before starting any measurements. This phase is indicated as "wait phase W". A suitable waiting time $t_w$ is about 0.2 sec.

As mentioned above, the camera 40 obtains at least two images, and these two images are compared with each other; for instance, these images are subtracted from each other. The camera may be a TV-camera, but preferably is a CCD-camera. For the further processing of the images obtained by the camera 40, an output of the camera 40 is coupled to an image processing device 50, which may be a standard image processing device or a suitably programmed computer. Since the nature and the construction of the image processing device 50 are not the subject of the present invention, and knowledge thereof will not be necessary for a skilled person for understanding the present invention, while further such image processing devices are known per se, this will not be discussed in further detail.

It will be evident to a skilled person that such image processing device 50 is able to "recognise" moving objects by comparing subsequent images. The object will be visible on only one of the images, or it will be visible on both images yet displaced; in both cases, subtracting the images will yield a strong object signal. However, experiments have shown that small glass particles, even if they are present in the field of view of the camera, do not necessarily at all times refract incoming light in such a way that outgoing light travels towards the camera. In other words: small glass particles appear not to be visible at all times.

According to the invention, this is understood as follows. The direction of the outgoing light depends on the shape of the glass particle and on the orientation of the glass particle with respect to the incoming light; due to the movement of the glass particle, said orientation changes, and therefore the direction of the outgoing light changes. It might be said that the light beam(s) emanating from such a moving glass particle "sweep" through space, now and then "hitting" the camera. If the images offered to the image processing device are obtained at moments in time when none of the light beams emanating from such a moving glass particle "hit" the camera, the particle is not detected. It is believed that a similar phenomenon plays a role in prior art techniques, and is at least partly responsible for the unsatisfying performance of prior art techniques in detecting small glass particles, especially those particles in the range of 0.2 mm–1 mm.

Based on the above-mentioned insight, the method for detecting glass particles according to the present invention has an improved detection reliability because the cycle of obtaining two images and comparing these two images is performed more than once. This is also illustrated in FIG. 2, where the moments in time where images $I_1$, $I_2$, $I_3$, etc. are provided are indicated as $t_{i1}$, $t_{i2}$, $t_{i3}$, etc. respectively. This phase is indicated as "repeated measurement phase RM".

In a preferred embodiment, which has proved to combine an excellent detecting reliability with an acceptable measuring time, said cycle is performed about 20 times. In each detecting cycle, comparing said two images yields a compared signal which is indicative for the presence of moving objects in the field of view of the camera. A bottle under investigation is rejected if in at least one of said detecting cycles the compared signal does indicate the presence of at least one moving object.

Thanks to said repeated detecting cycle, the chances that a particle is invisible to the camera in all images are decreased substantially.

Because of said repeated detecting cycle, the measuring time which is to be spent on any bottle under investigation is relatively long: in the order of about 1 sec. As mentioned above, during this measuring time the bottle under investigation must be held completely stationary with respect to the camera. In view of the fact that the invention relates to a health aspect, every bottle as produced by a production line is to be inspected for the presence of glass particles. On the other hand, the detection method should preferably be performed in such a way that the production capacity of such a production line is not decreased. At first sight, these requirements conflict with each other. However, the invention provides an apparatus for performing the detecting method, which meets all of said requirements.

Figure 3:
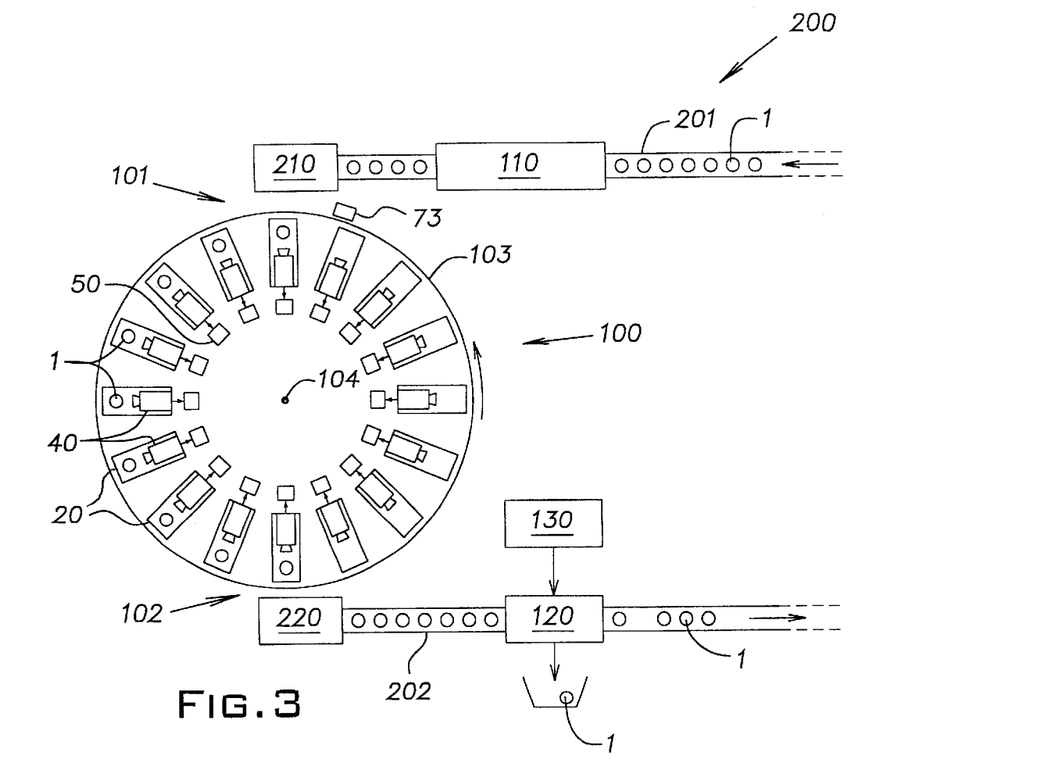
FIG. 3 is a schematical top view of a detection apparatus incorporated in a production line.

According to the invention, a detecting apparatus 100 comprises a plurality of detecting stations 20. Each of said detecting stations 20 comprises a camera 40 as described before, and is capable of accepting a bottle 1 at an entrance position 101, holding the bottle 1 for inspection, and delivering the inspected bottle 1 at an exit position 102. In a preferred embodiment, as illustrated in FIG. 3, the subframes 21 of the stations 20 are mounted on a second subframe 103 which is rotatably mounted with respect to the fixed world. The second subframe 103 can have the shape of a disk or a wheel, for instance, and will hereinafter be referred to as "carousel". The carousel 103 and the subframes 21 can be formed integrally as a single unit. The carousel 103 is rotated by means of rotation drive means which are not illustrated for the sake of simplicity.

FIG. 3 depicts schematically a part of a production line 200 for filling bottles 1 with beer. The filled bottles 1 are transported by a transportation means 201 to reach a spin/stop station 110, where the bottles 1 are spinned and subsequently halted, as described before. After the spin/stop station 110, the bottles 1 are fed to the entrance position 101 of the carousel 103, where they are introduced into respective measuring stations 20 by means of transfer means 210. From the entrance position 101, the station 20 with the bottle 1 follows part of the orbit around the rotational axis 104 of the carousel 103, to reach the exit position 102, where by means of a second transfer means 220, the bottle 1 is removed from the station 20 and transferred to a transportation means 202 for further handling. A reject station 120 is arranged, which is controlled by a control unit 130. The control unit 130 receives information from the image processing units 50, and controls the reject unit 120 for rejecting or passing bottles 1 based on the information obtained from the image processing units 50.

Because of the above arrangement, every bottle 1 can be investigated during a specific time during its stay on the carousel 103, while the number of bottles passing the carousel 103 per unit time is identical to the number of bottles produced by the process line 200 per unit time. In other words, the capacity of the process line 200 is unaffected.

In a preferred embodiment, the number of stations 20 per carousel is 24. For accomodating a measuring time of 0.7 sec, while allowing for a non-measuring time of about 0.7 sec, including input and output transfer times, the carousel 103 can have a rotation speed of around 43 revolutions per minute. Thus, the apparatus 100 according to the invention is capable of inspecting more than 60,000 bottles per hour. The above is based on a carousel diameter of about 85 cm, which can acceptably be accomodated in existing process lines.

For increasing the capacity of the apparatus 100, it is possible to increase the number of cameras per carousel; this will lead to an increase in the diameter of the carousel 103. As an alternative, one might increase the number of carousels. In this respect it is noted that, under the above-indicated circumstances, the spin-speed suitably has a value of about 1000 rpm, as mentioned. Should, however, a shorter or longer input transfer time appear to be necessary, the spin-speed may be adapted to optimise the flow characteristics of the fluid/particles in the bottle during the inspection time window.

The carousel 103 comprises a plurality of cameras 40 and a plurality of image processing units 50, each image processing unit 50 being dedicated to and connected to one camera 40. Power can be supplied to these instruments on board the rotating carousel 103 by means of slip contacts, as is known per se. The central processing unit 130 is arranged stationary, and is connected to the reject unit 120. It will be evident that the image processing units 50 can not be connected directly to the central control unit 130 for signal transfer; coupling by means of slip contacts is not preferred.

According to the invention, the communication path between the image processing units 50 and the central control unit 130 comprises a wireless path.

Figure 4:
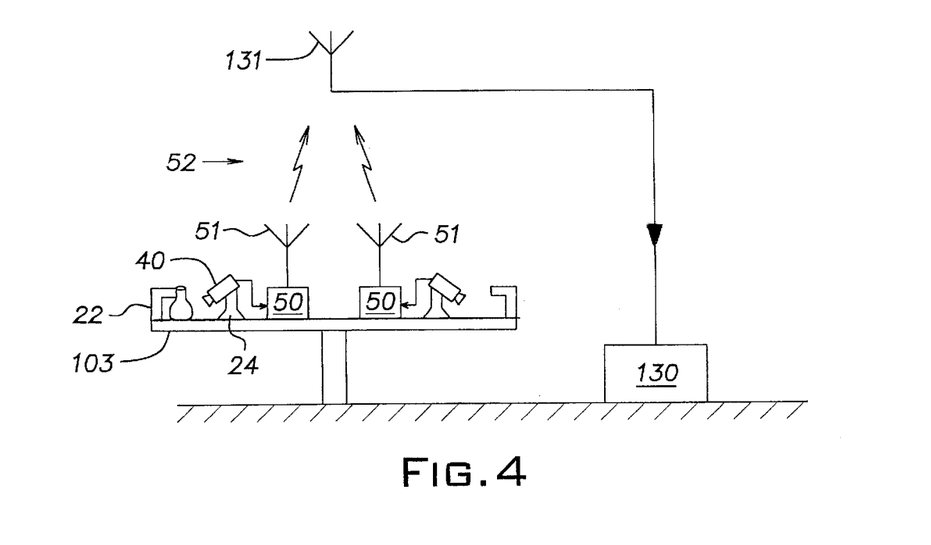
FIG. 4 is a schematical side view of a carousel, which schematically illustrates a method of data transfer.

In a possible embodiment, as schematically illustrated in FIG. 4, the image processing units 50 communicate with the CPU 130 by means of radio signals 52, which can be, for instance, frequency modulated, as is known per se. Each image processing unit 50 is associated with a transmitter 51 for transmitting suitably coded signals representing the "verdict" of the IPU 50 regarding the bottle 1 under investigation, and above the carousel 103 a receiver (antenna) 131 is arranged which is connected to an input of the CPU 130. The CPU 130 "knows" when this bottle 1 reaches the reject station 120, and, if necessary, sends a suitable reject signal to the reject station 120 for rejecting the bottle 1. The CPU 130 recognizes the identity of the different IPUs 50, for instance because each IPU's transmitter 51 uses an individual carrier frequency. It is also possible that the different IPUs are adapted to send their data after each other, so that at any moment in time at most one of the IPUs 50 is sending.

Figure 5:
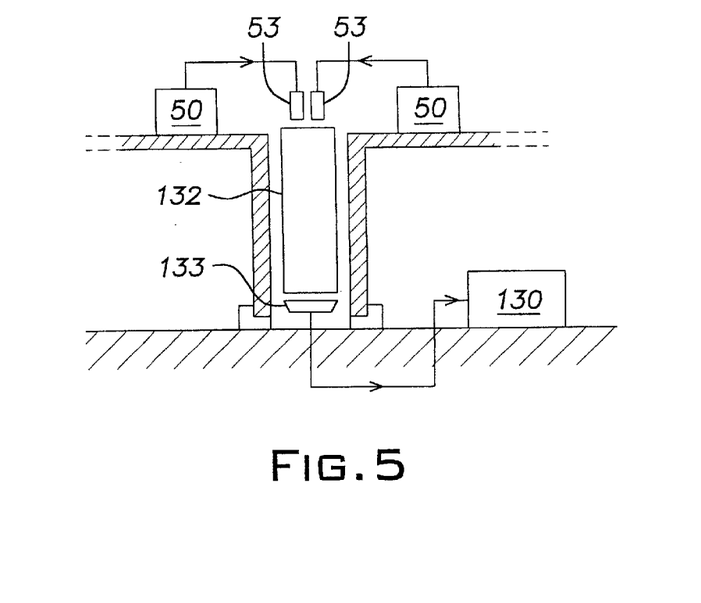
FIG. 5 is a schematical side view of a carousel, which schematically illustrates a preferred method of data transfer.

In a preferred embodiment, as schematically illustrated in FIG. 5, the image processing units 50 communicate with the CPU 130 by means of optical signals. The carousel 103 may suitably comprise an optical wave guide 132 which is mounted at the center of the carousel 103, coaxially with the rotational axis of the carousel 103. The optical wave guide 132 may be fixed with respect to the fixed world, i.e. the optical wave guide 132 may be arranged stationary, or the optical wave guide 132 may be fixed with respect to the carousel 103, i.e. the optical wave guide 132 may be arranged rotationary. Normally, the entrance side of the optical wave guide 132 will be the upper end. Each image processing unit 50 is provided with an optical transmitter 53 for sending optical signals into the optical wave guide 132. Opposite the other end of the optical wave guide 132, an optical receiver 133 is arranged stationary; this optical receiver 133 is connected to the CPU 130.

Again, the IPUs 50 may be adapted to send their data separated in time. It is also possible that the IPUs 50 send their data simultaneously via parallel paths, through one optical wave guide 132 or through parallel wave guides. Transmission by parallel wave guides is possible, for instance, by using ring-shaped detectors 133 arranged coaxially.

The wave guide medium may be, for instance, glass or air.

It is to be noted that the invention is not restricted to the above-mentioned exemplary signal transfer methods, and that other signal transfer methods, as will be apparent to skilled persons, may be used in the present invention, too.

As mentioned above, each bottle 1 is viewed by a camera 40, and each camera 40 is associated with an image processing unit 50. In the embodiment as described above, each camera 40 is associated with its own, dedicated IPU 50. According to a further aspect of the invention, it is possible to reduce the costs of the detecting apparatus by having two or more cameras 40 share one image processing unit 50. Thus, in an embodiment comprising 24 cameras, when two or four cameras 40 are connected to one and the same IPU 50, the number of IPUs on the carousel 103 need only be 12 or 6, respectively. In the following, some examples for cost reduction in this respect will be explained.

Figure 6A:
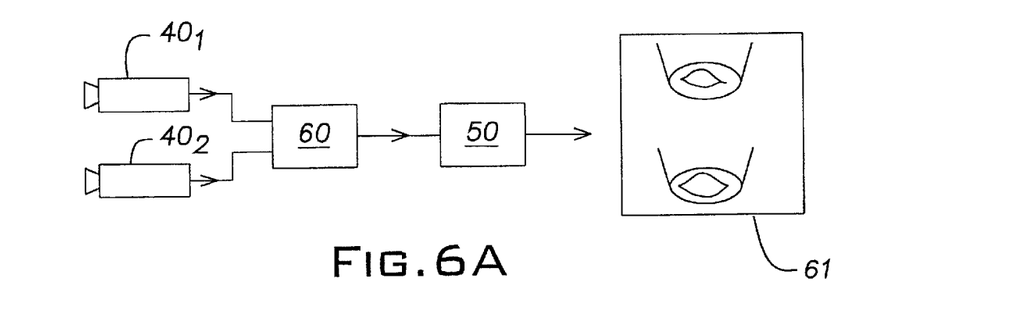
FIGS. 6A–B illustrates a cost efficient embodiment for the image processing scheme.

Because of the viewing angle of the camera 40, the scene of interest (i.e. the bottom half of a bottle 1) only takes a relatively small portion of the height of the image as produced by the camera 40. Thus, it is possible to project two of such scenes above each other in an image, as illustrated in FIG. 6A. In order to achieve this effect, the output signals of two cameras $40_1$, $40_2$ are fed to a multiplexer 60 which combines these two signals into a combined signal representing a combined image 61, such that the top half of the combined image 61 comprises the scene of interest of the first camera $40_1$ while the bottom half of the combined image 61 comprises the scene of interest of the second camera $40_2$.

The combined signal of the multiplexer 60 is fed to one image processing unit 50, which processes the signal as described before. In case a signal representing a glass particle is detected, the IPU 50 checks whether this signal is in the top half or in the bottom half of the image 61, in other words it investigates which camera and thus which bottle this signal is associated with, and sends the relevant information to the CPU 130.

A similar technique can be adapted for projecting two scenes of interest next to each other on one image. Combining such techniques as mentioned above results in four scenes being projected onto one image, which results in a reduction of the costs involved with the IPUs 50 by a factor four. This in turn simplifies the communication between the IPUs 50 and the CPU 130, because the required number of communication signals is likewise reduced.

It is noted, in this respect, that a multiplexer per se is already known, for instance for use in closed circuit television systems in order to have a plurality of images (as provided by a plurality of cameras) displayed on one monitor, as will be clear to persons skilled in the art. Also, in cable television systems, it is known to display the images of a plurality of channels on one screen (mozaic channel). Therefore, a detailed description of the multiplexer is omitted here.

Figure 6B:
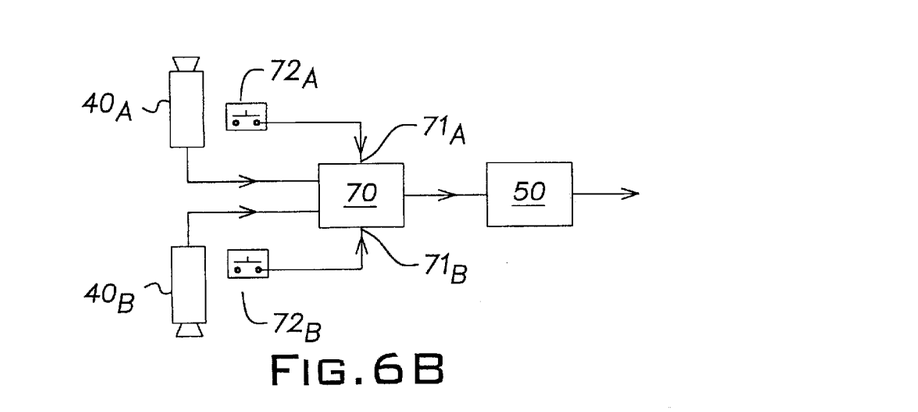

A further cost reduction in this respect is possible if each camera 40 is only actively involved in investigating a bottle 1 during half (or less) of the revolution cycle of the carousel 103, as illustrated in FIG. 3. If such is the case, a camera $40_B$ radially opposite an active camera $40_A$ will be inactive. According to the invention, these two opposite cameras $40_A$, $40_B$ can share an image processing unit 50. As illustrated in FIG. 6B, the signals of two opposite cameras $40_A$, $40_B$ are fed to a selector 70, which has position inputs 71 coupled to receive information regarding the position of the carousel 103. In a relatively simple embodiment, each camera $40_A$, $40_B$ is associated with a switch $72_A$, $72_B$ which cooperates with a reference actuator 73 (mechanically, optically, electro-magnetically, etc) arranged stationary adjacent the carousel 103 at a position near the entrance position 101. Each time the selector 70 receives a signal at his position input $71_A$, $71_B$, it selects the signal of the corresponding camera $40_A$, $40_B$ and passes this signal to the image processing unit 50, the signal of the opposite camera $40_B$, $40_A$ being ignored.

By combining the above-mentioned techniques, a carousel having 24 cameras needs only have 3 image processing units.

The invention also provides a reduction of the memory size necessary for the image processing units for being able to process the signals from the cameras, as will be explained in the following.

As is well known in the art, TV cameras generate a signal which describes an image by means of scan lines in an interlaced manner. An image is represented by a large number of horizontal lines, which can be numbered successively as 1, 2, 3, 4, etc. from top to bottom. However, these lines are not scanned in this order. A first half-image (odd half-image) is formed by successively scanning the odd lines 1, 3, 5, 7, etc; in European cameras, this takes about 20 ms. Subsequently, a second half-image (even half-image) is formed by successively scanning the even lines 2, 4, 6, 8 etc. Thus, scanning the complete image information takes about 40 ms. After this, the above mentioned process is repeated.

In the following, the number of lines in the image will be indicated by L, and the number of picture elements (pixels) in each line will be indicated by P. Ordinarily, for performing the comparison technique between subsequent images, an image processor needs a memory of at least L×P memory elements. This memory is firstly filled with the scanned information of a first image, i.e. both the odd half-image and the even half-image of the first image. Then, the first pixel of the first line is scanned again; just before this informatation is stored into the corresponding memory element, it is compared with the information already present therein. This process is repeated for all pixels of the first line, then for all pixels of the third line, etc. After 40 ms, a new image will have been stored in the memory, and the comparison with the previous image will then have been completed. It can easily be seen, that the comparison process thus takes 40 ms (or the bottles are investigated with an investigation frequency of 25 Hz).

According to the invention, it is possible to reduce the memory needed to ½×L×P, and to reduce the time for the comparison process to 20 ms (or increase the investigation frequency to 50 Hz), by performing an interlaced comparison, as follows. First, the odd half-image of the first image is stored in the memory, which takes about 20 ms. Then, the first pixel of the second line is scanned, and stored in the memory element where previously the first pixel of the first line was stored. However, just before storage, the first pixel of the second line is compared with the average of the first pixel of the first line and the first pixel of the third line. This process is repeated for all pixels of the second line, then for all pixels of the fourth line, etc. After 20 ms, the second half-image will have been stored in the memory, and the comparison with the previous half image will then have been completed.

It can easily be seen that the comparison process thus takes 20 ms. It can further easily be seen that the inspection process of one bottle can be performed 50 times in one second.

In other words, on a pixel-by-pixel base, a new image is not really compared with the previous image but a half-image is compared with an estimate based on the previous half-image. However, this comparison process does obtain reliable results, thanks to the fact that light emanating from stationary items usually illuminates more than one pixel.

As will be evident to a person skilled in the art, variations and modifications to the embodiment as described will be possible without leaving the inventive concept or the scope of protection as defined in the claims. For instance, with respect to the embodiment as illustrated in FIG. 6B, in case a camera is only actively involved in investigating a bottle during a third, or a fourth etc. part of the revolution cycle of the carousel 103, it is possible to feed the signal from three or four etc. cameras subsequently to one image processing unit.

What is claimed is:

1. Method of detecting the presence of glass particles in a bottle filled with a beverage, the bottle (1) having a bottom (4) with a central, inwardly directed convex portion (6), and also having a longitudinal axis (13); the method comprising the steps of:

a) causing the beverage (10) in the bottle (1) to rotate with respect to the bottle (1);

b) holding the bottle (1) stationary with respect to a camera (40);

c) illuminating the bottle (1) with a light bundle (31) impinging on the bottom (4) of the bottle (1), said light bundle (31) being directed substantially parallel to said longitudinal axis (13) of the bottle (1);

d) directing the camera (40) such that an optical axis (41) of the camera (40) makes an angle α in the range of 120°–150° with the direction (32) of the bundle (31);

e) obtaining a first image signal representative for a first image obtained by the camera (40) at a time $t_1$ when a present glass particle is in a first position and a first orientation within said bottle;

f) obtaining a second image signal representative for a second image obtained by the camera (40), the second image being obtained at a moment in time $t_2$ subsequent the moment in time $t_1$, said glass particle being in a second position and a second orientation within said bottle;

g) comparing the first and second image signals to obtain a first compared signal;

h) obtaining a third image signal representative for a third image obtained by the camera (40) at a moment in time $t_3$ subsequent the moment in time $t_2$, said glass particle being in a third position and a third orientation within said bottle;

i) obtaining a fourth image signal representative for a fourth image obtained by the camera (40) at a moment in time $t_4$ subsequent the moment in time $t_3$, said glass particle being in a fourth Position and a fourth orientation within said bottle;

j) comparing the third and fourth image signals to obtain a second compared signal;

k) generating a bottle reject signal if at least one of the compared signals obtained in step (g) or step (j) indicates the presence of a moving object.

2. Method according to claim 1, wherein the bottle is filled with a $CO_2$ containing beverage such as beer, the method at least being capable of detecting glass particles (12) in the range of 0.2 mm to 10 mm.

3. Method according to claim 1, wherein step (a) comprises the steps of:

(a1) accelerating the bottle (1) with a substantially constant acceleration during a time interval of 0.05–0.2 sec to reach a spin speed of 500–2000 revolutions per minute;

(a2) maintaining the spin speed constant at said value for about 0.5–1.5 sec;

(a3) decelerating the bottle (1) with a substantially constant deceleration to stop in a time interval of 0.05–0.2 sec.

4. Method according to claim 3, wherein after the bottle (1) has come to a stop, a time $t_w$ lapses before commencement of step (e).

5. Method according to claim 1, wherein the steps (e)–(g) are repeated to a total of 10–30 times.

6. Method according to claim 2, wherein step (a) comprises the steps of:

(a1) accelerating the bottle (1) with a substantially constant acceleration during a time interval of 0.05–0.2 sec to reach a spin speed of 500–2000 revolutions per minute;

(a2) maintaining the spin speed constant at said value for about 0.5–1.5 sec;

(a3) decelerating the bottle (1) with a substantially constant deceleration to stop in a time interval of 0.05–0.2 sec.

7. Method according to claim 6, wherein after the bottle (1) has come to a stop, a time $t_w$ lapses before commencement of step (e).

8. A method according to claim 1, wherein at least one additional compared signal is generated by obtaining at least fifth and sixth image signals at moments in time $t_5$ and $t_6$ respectively, wherein each additional compared signal is obtained by comparing two independently obtained image signals, said image signals being obtained respectively at separate, discretely spaced moments in time.

9. A method according to claim 1, wherein step (b) further comprises a waiting period, said waiting period being of sufficient length in time to allow small glass particles having a mean diameter of less than approximately 0.2 mm to migrate from the perimeter of said convex portion to the top thereof as resulting from pressure-induced flow within the beverage.

10. A production line (200) for filling bottles (1) with a beverage, each bottle (1) having a longitudinal axis (13) and a bottom (4) having a central, inwardly directed convex portion (6); the production line (200) comprising a detecting apparatus, a first transportation means (201) for transporting the filled bottles (1) towards the detecting apparatus (100), and a second transportation means (202) for transporting the checked bottles (1) away from the detecting apparatus (100); the detecting apparatus (100) comprising:

a carousel (103) which is rotatably mounted with respect to the fixed world;

a plurality of detecting stations (20) fixed to said carousel (103), each detecting station (20) comprising:

a subframe (21);

holding means (22) for accepting and holding a bottle (1) in an upright position stationary with respect to said subframe (21);

an illumination device (30) for generating a bundle of visible light (31), said light bundle (31) being directed substantially parallel to said longitudinal axis (13) of an accepted bottle (1) held by said holding means (22);

a camera (40) fixed to said subframe (21), an optical axis (41) of the camera (40) being directed such that it makes an angle α in the range of 120° to 150° with the direction (32) of the bundle (31) and intersects the central axis (13) of said accepted bottle (1) at a point S which is located near the top of the hill portion (6), said camera (40) being adapted to obtain first, second, third, and fourth image signals respectively at subsequent moments in time $t_1$, $t_2$, $t_3$, and $t_4$;

the apparatus (100) further comprising:

at least one image processing unit (50), a central processing unit (130), and a reject device (120) associated with said second transportation means (202), each image processing unit (50) being adapted to receive said first, second, third, and fourth image signals from said camera (40), to compare said first and second image signals to provide a first compared signal, to compare said third and fourth image signals to provide a second compared signal, and to communicate said first and second compared signals to said central processing unit (130), said central processing unit (130) being adapted to control said reject device (120) such as to remove rejected bottles from said second transportation means (202) if at least one of said compared signals indicates the presence of a moving object.

11. Product line according to claim 10, wherein the detecting apparatus (100) is adapted to examine at least 60,000 bottles per hour.

12. Production line according to claim 10, wherein the camera (40) is set such that its focal point or focal plane substantial coincides with said point S.

13. Production line according to claim 12, wherein the outputs of two oppositely mounted cameras ($40_A$, $40_B$) are fed to a selector (70), which is adapted to select the signal from an active camera and to provide the selected signal to one image processing unit (50).

14. Production line according to claim 12, wherein the outputs of at least two cameras ($40_1$, $40_2$) are coupled to a multiplexer (60) which is adapted to combine these signals into a combined signal representing a combined image (61), and to provide the combined signal to one image processing unit (50).

15. Production line according to claim 14, wherein the outputs of two oppositely mounted cameras ($40_A$, $40_B$) are fed to a selector (70), which is adapted to select the signal from an active camera and to provide the selected signal to one image processing unit (50).

16. Production line according to claim 10, wherein each image processing unit (50) is fixed to said carousel (103), and wherein said central processing unit (130) is mounted stationary.

17. Production line according to claim 16, wherein each image processing unit (50) communicates with said central processing unit (130) by radio signals.

18. Production line according to claim 16, wherein each image processing unit (50) communicates with said central processing unit (130) by optical signals.

19. Production line according to claim 18, wherein each image processing unit is coupled to an optical transmitter (53) which is arranged near the rotational axis of the carousel (103), the central processing unit (130) being coupled to an optical receiver which is arranged near the rotational axis of the carousel (103).

20. Production line according to claim 10, wherein the outputs of at least two cameras ($40_1$, $40_2$) are coupled to a multiplexer (60) which is adapted to combine these signals into a combined signal representing a combined image (61), and to provide the combined signal to one image processing unit (50).

21. Production line according to claim 20, wherein the outputs of two oppositely mounted cameras ($40_A$, $40_B$) are fed to a selector (70), which is adapted to select the signal from an active camera and to provide the selected signal to one image processing unit (50).

22. Production line according to claim 10, wherein the outputs of two oppositely mounted cameras ($40_A$, $40_B$) are fed to a selector (70), which is adapted to select the signal from an active camera and to provide the selected signal to one image processing unit (50).

23. Production line according to claim 10, wherein the camera (40) is adapted to obtain a first half image and a second half image, the first half image being obtained by scanning the odd lines of the image of a bottle to be inspected and the second half image being obtained by scanning the even lines of the image of said bottle; each image processing unit (50) being adapted to compare a pixel of an image line of the second half-image with the average of the pixels of image lines of the first half-image, which pixels are located on the odd lines directly above and directly below said pixel on the even line of the second half-image.

24. A detecting apparatus comprising:
a carousel (103) which is rotatably mounted with respect to the fixed world;
a plurality of detecting stations (20) comprising:
a subframe (21);
holding means (22) for accepting and holding a bottle (1) in an upright position stationary with respect to said subframe (21), said bottle (1) having a longitudinal axis (13);
an illumination device (30) for generating a bundle of visible light (31), said light bundle (31) being directed substantially parallel to said longitudinal axis (13) of an accepted bottle (1) held by said holding means (22);
a camera (40) fixed to said subframe (21), an optical axis (41) of the camera (40) being directed such that it makes an angle α in the range of 120° to 150° with the direction (32) of the bundle (31) and intersects the central axis (13) of said accepted bottle (1) at a point S which is located near the top of the hill portion (6), said camera (40) being adapted to obtain first, second, third, and fourth image signals respectively at subsequent moments in time $t_1$, $t_2$, $t_3$, and $t_4$, said first and second image signals being capable of comparison to provide a first compared signal, said third and fourth image signals being capable of comparison to provide a second compared signal, said first and second compared signals being capable of analysis to generate a bottle reject signal if at least one of said compared signals indicates the presence of a moving object.

25. A detecting apparatus according to claim 24, wherein each image processing unit (50) is fixed to said carousel (103), and wherein said central processing unit (130) is mounted stationary.

* * * * *

UNITED STATES PATENT AND TRADEMARK OFFICE
CERTIFICATE OF CORRECTION

PATENT NO. : 6,275,603 B1
DATED : August 14, 2001
INVENTOR(S) : Anthony James Cronshaw et al.

It is certified that error appears in the above-identified patent and that said Letters Patent is hereby corrected as shown below:

<u>Title page,</u>
Under *Primary Examiner*, delete "Mancus" and insert therefore -- Mancuso --.

<u>Column 1,</u>
Lines 5-6 delete "as for example disclosed in U.S. Pat. No. 3,777,169,".
Line 11, after "methods" insert -- , as for example disclosed in US-A-3,777,169, --.

Signed and Sealed this

Ninth Day of April, 2002

Attest:

JAMES E. ROGAN
*Director of the United States Patent and Trademark Office*

*Attesting Officer*